United States Patent [19]

Reynolds

[11] 4,441,485
[45] Apr. 10, 1984

[54] MOVEMENT DAMPENING EAR SPECULUM

[76] Inventor: William V. Reynolds, 375 Main St., Oneonta, N.Y. 13820

[21] Appl. No.: 261,364

[22] Filed: May 7, 1981

[51] Int. Cl.³ .............................................. A61B 1/22
[52] U.S. Cl. ......................................... 128/9; 269/1; 128/303 R
[58] Field of Search ............ 128/9, 3, 4, 12, DIG. 26, 128/329 R; 269/1; 128/303 R, 343

[56] References Cited

U.S. PATENT DOCUMENTS

| 3,020,912 | 2/1962 | Chester | 128/9 X |
| 3,338,538 | 8/1967 | Roche | 128/DIG. 26 X |
| 3,374,791 | 3/1968 | Westerman | 128/4 X |

Primary Examiner—Michael H. Thaler
Attorney, Agent, or Firm—Clarence F. Stanback, Jr.

[57] ABSTRACT

An inexpensive and disposable surgical unit designed preferably for use during ear surgery. The unit includes an ear speculum with a coiled-spring located therein to steady a surgical instrument which extends through the coils of the coiled-spring to thereby avoid damage to the ear by uncontrolled movements of the surgeon.

7 Claims, 2 Drawing Figures

MOVEMENT DAMPENING EAR SPECULUM

BACKGROUND OF THE INVENTION

1. Field of the Invention

This invention relates to a device for aiding the surgeon while performing an operation on a human ear and more particularly to a device for avoiding damage to the ear by uncontrolled movement by the surgeon.

2. Description of the Prior Art

Various devices are known for preventing damage to the ear during surgery. A device for preventing hazards during a myringotomy or a similar operation is described in U.S. Pat. No. 3,020,912. The device includes a battery powered motor for providing rotary motion to a surgical knife through a set of drive gears. The operation of this device is complicated because of the motor drive and the gearing. Moreover, it is bulky because of the addition of a battery pack for powering the motor.

During ear surgery, the foregoing device is attached to an ear speculum at its wide funnel-shaped opening and the surgical knife extends therethrough and out of the tapered end of the speculum into the inner ear. The surgical knife is supported by a plurality of ball bearings to prevent wobble and friction. One of the plurality of bearings is mounted on the inner wall of the speculum. This bearing is semi-circular in shape and forms a cradle to support the rotating surgical blade and to prevent the blade from wobbling.

Although the motor driven surgical knife is functional and prevents wobble, it is not cost effective because of the need for batteries, a motor and associated gearing, bearings and complicated attachments. Furthermore, the device is too expensive to be disposed of after each use in surgery.

OBJECTS OF THE INVENTION

It is an object of the present invention to provide a surgical device that is simple in construction and that is capable of controlling the movements made by the surgeon during an ear operation.

It is another object of the present invention to provide a surgical device that can be constructed from relatively inexpensive materials.

A further object of the present invention is to provide a surgical device that can be discarded after each use in surgery.

SUMMARY OF THE INVENTION

The foregoing objects are accomplished through the use of a surgical unit for the ear that is designed to be both inexpensive and disposable after each use. The surgical unit includes a speculum fabricated from plastic and a coiled spring, fabricated preferably from plastic, for steadying the surgical instrument that extends therethrough. The length of the coiled-spring conforms to the inner diameter of the speculum. During surgery the surgical unit can be held firmly in place by strips of adhesive tape placed over the wide outer rim of the speculum and pressed onto both the neck, posteriorly, and the face of the patient.

The foregoing and other objects, features and attendant advantages of the invention will be apparent from the following more particular description of the preferred embodiment of the invention as illustrated in the accompanying drawings.

DESCRIPTION OF THE PREFERRED EMBODIMENT

Figure 1:
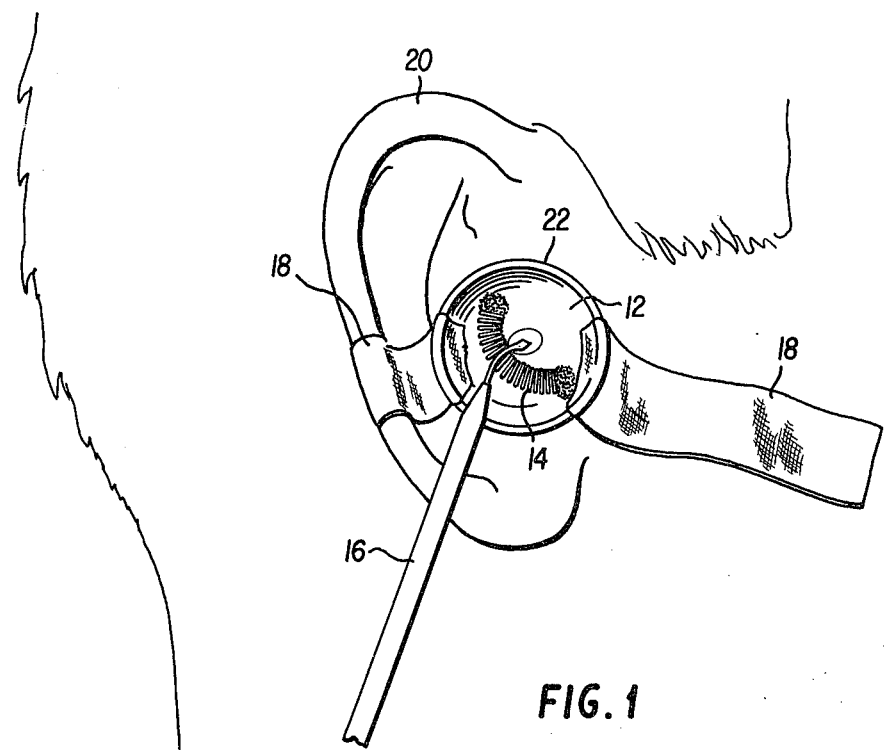
FIG. 1 is an enlarged elevation view of the surgical unit of the present invention illustrating the relationship between the several components thereof.

Referring to FIG. 1, the surgical unit of the invention comprises the combination of a speculum 12, a coiled-spring 14, a surgical instrument 16 and adhesive strips 18 for holding the speculum 12 in intimate contact with the ear 20 in which the operation is to be performed.

Figure 2:
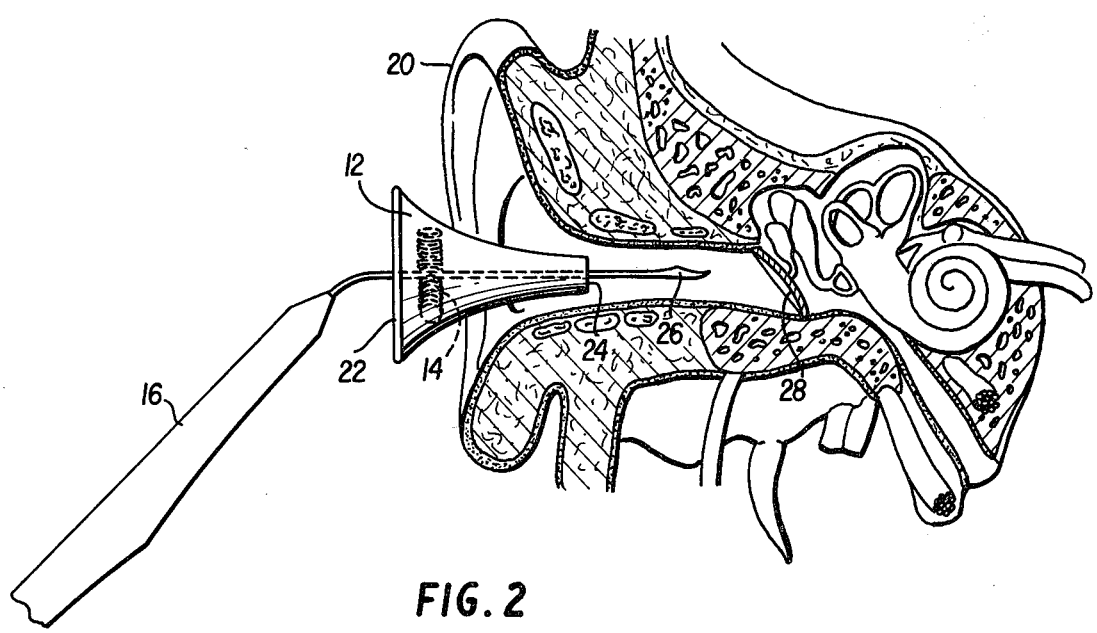
FIG. 2 is a side view in elevation of the surgical unit of FIG. 1 with the human ear being in cross-section.

The speculum 12 is made of a plastic material designed particularly for ear surgery under magnification with an operating room microscope (not shown). The speculum has a conventional funnel-shape as seen more particularly in FIG. 2. The wider end 22 of the speculum 12 rests against the outer portion of the ear, whereas the tapered portion 24 of the speculum is inserted into the inner portion of the ear canal. As seen in FIG. 2, the moving edge 26 of the surgical instrument 16 extends through the tapered portion 24 of the speculum into the ear canal adjacent the eardrum 28.

The coiled-spring 14 is preferably made of plastic and is relatively inexpensive. As illustrated in FIG. 1, the lengthwise extension of the coiled-spring conforms to the inner diameter of the speculum. In addition, the coils of the coiled-spring are of a lesser diameter than the diameter of the opening at the tapered end 24 of the speculum 12.

As stated previously, the foregoing surgical unit is used during surgery on the ear. To be more specific, the speculum and coiled-spring unit is ideally suited for operating on the eardrum, middle ear or for operating on the sheath of the facial nerve or inner ear.

During surgery on the ear, the speculum 12 and the coiled-spring 14 are held stationary against the ear by adhesive strips 18. With the aid of a microscope (not shown), surgery can be performed. The surgical instrument 16 is inserted between the coils of the coiled-spring 14. The coils secure the surgical instrument 16 against unwanted movements made by the operating surgeon. If microsurgery is performed without the aid of a device such as the disclosed surgical unit, the natural tremors or involuntary movements of the hands of the surgeon may cause damage to the structures of the ear. For example, sudden inward or lateral movements of the surgical instrument 16 are impeded by the coils. The voluntary movements made by the operating surgeon are enhanced by the control provided by the coils of the coiled-spring.

The coiled-spring 14 is described above as being made of plastic. However, it should be noted that it can be fabricated from other materials (e.g., metal) and still function to secure the surgical instrument during surgery.

It is to be understood that one form of this invention has been illustrated and described and that it is not to be limited to the specific form or arrangement of parts herein described and shown except insofar as such limitations are included in the claims.

Other microsurgical applications for the surgical unit are possible (e.g., eye surgery, suturing of tendon, nerve sheaths and paranasal sinuses, etc.). Consequently, the features of the apparatus may be changed or varied in lesser or greater degree without departing from the essence of the invention defined in the following claims.

Further, the invention may also be used in industry for assembling minute structures as in computer components, hearing aids or watch making.

What I claim and desire to be secured by Letters Patent of the United States is:

1. A surgical unit for the human ear, comprising:
    a speculum for insertion into the human ear;
    a coiled-spring attached to the inner wall of said speculum; said coiled-spring extending circumferentially within said speculum and conforming to the inner circular wall of said speculum;
    means for securing the speculum in intimate contact with the human ear; and
    a surgical instrument extending through said speculum and inserted between the coils of said coiled-spring to an area of the ear where surgery is to be performed; said coils of said coiled-spring supporting said surgical instrument to impede sudden involuntary inward and lateral movements made by an operating surgeon to thereby prevent damage to the ear, and said coils of said coiled-spring controlling the voluntary movements of the operating surgeon to thereby enhance the operation and increase the success rate of the surgery.

2. A surgical unit as in claim 1 wherein said coiled-spring is an integral portion of said speculum.

3. A surgical unit as in claim 1 wherein said speculum and said coiled-spring are fabricated from plastic.

4. A surgical unit as in claim 3 wherein said speculum and said coiled-spring are disposed of after surgery.

5. A surgical unit as in claim 1 wherein said speculum and said coiled-spring are fabricated from metal.

6. A surgical unit as in claim 1 wherein the coils of said coiled-spring are of a diameter less than the smallest inner diameter of said speculum.

7. A surgical unit as in claim 1 wherein said surgical unit is adapted for microsurgery on the human ear.

* * * * *